US009168528B2

(12) United States Patent
Hassouneh et al.

(10) Patent No.: US 9,168,528 B2
(45) Date of Patent: Oct. 27, 2015

(54) FLUIDS CONCENTRATION CUP ASSEMBLY WITH HOURGLASS SHAPE

(71) Applicant: Alliance Partners LLC, San Antonio, TX (US)

(72) Inventors: Emad Hassouneh, San Antonio, TX (US); Logan White, Garfield Heights, OH (US); Matt Schmidt, San Antonio, TX (US); Frank Morris, Austin, TX (US); Andrew Enke, San Antonio, TX (US)

(73) Assignee: Alliance Partners, LLC, San Antonio, TX (US)

( * ) Notice: Subject to any disclaimer, the term of this patent is extended or adjusted under 35 U.S.C. 154(b) by 0 days.

(21) Appl. No.: 14/242,219

(22) Filed: Apr. 1, 2014

(65) Prior Publication Data

US 2015/0004080 A1    Jan. 1, 2015

Related U.S. Application Data

(60) Provisional application No. 61/807,519, filed on Apr. 2, 2013, provisional application No. 61/880,500, filed on Sep. 20, 2013.

(51) Int. Cl.
*B01L 3/00* (2006.01)
*A61B 10/00* (2006.01)

(52) U.S. Cl.
CPC ............. *B01L 3/508* (2013.01); *B01L 3/5021* (2013.01); *A61B 10/0096* (2013.01); *B01L 2300/0858* (2013.01); *B01L 2400/0409* (2013.01); *B01L 2400/0478* (2013.01)

(58) Field of Classification Search
CPC .................. G01N 33/491; G01N 2035/00495; B01D 17/0217
See application file for complete search history.

(56) References Cited

U.S. PATENT DOCUMENTS

| 602,780 A | | 4/1898 | Stokes |
| 3,513,976 A | * | 5/1970 | James ........................... 210/782 |
| 3,911,918 A | | 10/1975 | Turner |
| 4,152,270 A | | 5/1979 | Cornell |
| 4,861,477 A | * | 8/1989 | Kimura ......................... 210/359 |
| 5,137,031 A | | 8/1992 | Guirguis |

(Continued)

FOREIGN PATENT DOCUMENTS

| EP | 2495302 A2 | 5/2012 |
| JP | 2002291874 | 8/2002 |

(Continued)

OTHER PUBLICATIONS

Blaine R. Copenheaver; Notification of Transmittal of the International Search Report and the Written Opinion of the International Searching Authority, or the Declaration; PCT/US2014/032502; Date of Mailing Aug. 22, 2014; 11 pages.

*Primary Examiner* — Paul Hyun
(74) *Attorney, Agent, or Firm* — Greenberg Traurig, LLP; Ross Spencer Garsson

(57) ABSTRACT

A biological fluid collection cup for use with a centrifuge bucket to separate a biological fluid into its component parts is disclosed. It includes an hourglass shape with a large upper and lower portion and a narrow middle portion. A piston is to slide into and slideably be received in the lower portion and a side port is provided for withdrawal of a fluid from the narrow portion.

21 Claims, 11 Drawing Sheets

PARTIAL DEPLOYED

(56) References Cited

U.S. PATENT DOCUMENTS

| | | |
|---|---|---|
| 5,393,674 A | 2/1995 | Levine et al. |
| 5,422,018 A | 6/1995 | Saunders et al. |
| 5,474,687 A | 12/1995 | Van Vlasselaer |
| 5,523,004 A | 6/1996 | Tanokura et al. |
| 5,550,060 A | 8/1996 | Saunders et al. |
| 5,674,458 A | 10/1997 | Holm |
| 2006/0273050 A1* | 12/2006 | Higgins et al. ............. 210/787 |
| 2007/0131612 A1* | 6/2007 | Duffy et al. ............. 210/600 |
| 2010/0140182 A1 | 6/2010 | Chapman et al. |
| 2010/0256595 A1 | 10/2010 | Leach et al. |

FOREIGN PATENT DOCUMENTS

| | | |
|---|---|---|
| KR | 1011250730000 | 3/2012 |
| KR | 1012895350000 | 7/2013 |
| WO | 2013100700 A1 | 4/2013 |

* cited by examiner

PARTIAL DEPLOYED

FLUIDS CONCENTRATION CUP ASSEMBLY WITH HOURGLASS SHAPE

This is a utility patent application claiming priority from and the benefit of U.S. Provisional Patent Application Ser. No. 61/807,519, filed Apr. 2, 2013; and U.S. Provisional Patent Application Ser. No. 61/880,500, filed Sep. 20, 2013, both of which are incorporated herein by reference.

FIELD OF THE INVENTION

Biological fluid concentration assembly, namely, a fluid concentration cup assembly with an hourglass shape, a drive piston, and a side draw fluid removal port.

BACKGROUND OF THE INVENTION

Biological fluid collection and concentration devices are known. Biological fluids, such as whole blood or bone marrow aspirate, may be collected and concentrated in an assembly, including a cup placed in a centrifuge, so as to separate out the biological fluid components by differing densities. Following centrifugation, a selected part or parts of the now separated biological fluid may be selected for removal from the concentration assembly. Typically, transfer of the biological fluid into the cup and removal after centrifugation of the selected biological fluid from the cup, which is subject to centrifugation, is typically accomplished through the top of the vessel.

SUMMARY OF THE INVENTION

A fluids concentration cup assembly is disclosed having a cup with an open top to which a lid is removably engaged and an open bottom, which receives a moveable piston therein, in one embodiment, a bottom plate, and, in one embodiment, a piston drive screw. The walls of the cup include an upper portion, a lower portion, and a narrowed portion between the upper and lower portions. The upper and lower portions are typically cylindrical and part of the narrow portion may be cylindrical. In the narrowed portion, a side port, generally perpendicular to a longitudinal axis of the cup, is provided for the side draw of a separated fluid out of the collection cup following centrifugation of the biological fluid in the cup.

In one embodiment of Applicant's device, the lid is configured for engaging a device, such as a syringe, to inject aspirate or biological fluid, such as whole blood or bone marrow aspirate, into the cup through the lid. After centrifuging, a moveable piston may be manually pushed or screw driven from the bottom up until a selected layer of the differentiated biological fluid is located adjacent the side port. A concentrate withdrawal device (such as a syringe) may be engaged with the side port for removal of the selected fluid. The proper fluid level is selected by pushing up the piston. In one embodiment, the selected fluid is buffy coat.

Another embodiment of the biological fluids concentration cup assembly may include a drive piston assembly where the drive piston assembly includes a drive piston slideably engaging the lower portion of the cup and coupling threaded members, one manually rotated by the user and the other engaging the piston. Rotation of the one causes the piston to move up and down in the cup.

A bottom plate may be provided for engaging the open bottom of the cup. The drive piston assembly may include a piston screw drive assembly for moving the piston longitudinally in the lower portion. The piston of the drive piston assembly includes a perimeter for fluid sealing against the walls off the cup, an upper and a lower surface, and wherein the lower surface may have a threaded member depending therefrom. The piston screw drive assembly includes a piston drive screw extending partly within the bottom portion of the cup to engage the depending threaded member and partly without the bottom plate. The piston drive screw goes through to the bottom plate through an aperture in the bottom plate. The piston drive screw has a base with a rim or perimeter, the base laying outside the bottom plate and adjacent thereto. Rotating the base causes the piston to rise up and down, forcing the concentrated (centrifuged) fluid above the piston to rise and fall with respect to the sideport. This allows selective withdrawal of fluid from the sideport.

DETAILED DESCRIPTION OF THE PREFERRED EMBODIMENT

Figure 1:
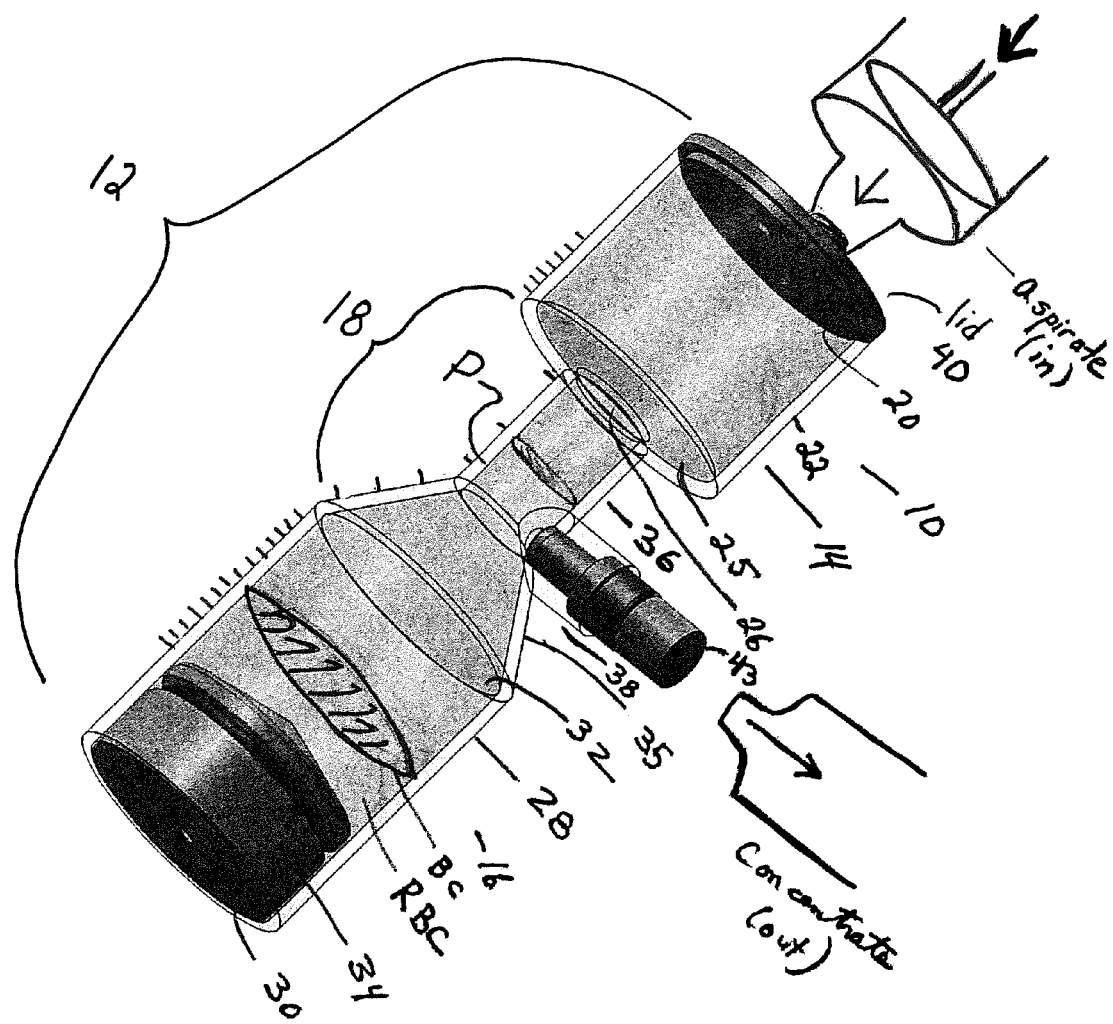
FIG. 1 is a perspective view of Applicant's fluids concentration cup assembly.

Applicant provides a first embodiment of a fluids concentration assembly 10, which includes a cup 12 with an open top 20 having a lid 40 engageable thereof and a slideable piston 34 engageable with an open bottom 30 thereof.

In one embodiment, Applicant's cup includes an upper portion 14, a lower portion 16, and a narrow portion 18. Upper portion 14 is seen to have a general cylindrical shape, with side walls 22 and an open top 20. Lower portion 16 is seen to be generally cylindrical and having side walls 28, an open bottom 30, which is adapted to slideable receive piston 34 therein. Narrow portion 18 may include sloped or cone-shaped top walls 25, through opening 26, a cylindrical waist portion 36, and sloped or cone-shaped bottom walls 35.

Narrow portion 18 is seen to have walls defining a diameter or diameters that are less than those defining the upper and/or lower portion. Thus, the term "narrow portion" is, typically referring to a general cylindrical portion with a wider portion below and a wider portion above. The narrowed portion may include only sloped walls 25/35 in one embodiment or mixed slanted and generally cylindrical portions. By providing a narrow portion, the vertical dimension or may have longitudinal dimension of a given fluid displaced by piston 34 moving upward in the lower portion is magnified. That is to say, one milliliter of fluid displaced upward in lower portion 16 is exaggerated, in a vertical dimension by movement of the fluid up through the constricted walls of the narrow portion. Thus, a thin layer, such as a buffy coat layer BC, between a red blood cell RBC layer and plasma P, below and above buffy coat, respectively, may be exaggerated (see FIG. 1), when BC comes up into the narrowed portion and lies adjacent a side port 38.

In one embodiment, lower portion 16 is integral with bottom walls 35, which may have open top 32. In one embodiment of Applicant's cup 12, side port 38, which includes walls adapted to engage a collection vessel for concentrate out (see arrows, FIG. 1), is adapted to be located near the bottom of waist portion 36, where it engages the open apex of bottom walls 35. Red blood cells then buffy coat may be drawn off when a buffy coat layer reaches above the top edge of side port 38. The piston is pushed up (by hand or any suitable device) until the lower boundary of the buffy coat layer (the buffy coat/red blood cell boundary) is positioned and then the side port 38 may be opened to allow removal of the buffy coat and/or the selected portion of the other fluids therefrom. A cap 43 may be provided to the side port so that when the collection device is not engaged, no fluid will flow out.

Scale lines are seen marked along the side of the outer walls of the container. They may be used to determine the volume of fluid and of the respective portions of separated concentrate. It will be seen that the gap between equal fluid markings will be larger where the volume is narrower or narrows, as the vertical axis if magnified of a fluid volume as it moves from the lower portion of the cone into the waist portion.

In a second preferred embodiment (FIGS. 2-6B), Applicant provides a fluids concentration assembly 110, which includes a cup 112 with an open top 120 having a lid 140 engageable therewith and a slideable piston 134 engageable with an open bottom 130 thereof of a lower portion 116.

In one embodiment, Applicant's cup includes an upper portion 114, lower portion 116, and/or a recessed or narrow portion 118. Narrow portion 118 may include sloped or cone-shaped top walls 118a and sloped or cone-shaped bottom walls 118b. Upper portion 114 is seen to have a general cylindrical shape, with side walls 122, and open top 120. Lower portion 116 is seen to be cylindrical and having side walls 128 and open bottom 130, which is adapted to receive slideable piston 134 therein.

Narrow or recessed portion 118 is seen to have walls defining a diameter or diameters that are less than those defining upper 114 and/or lower portion 116. Narrow portion 118 may include top walls 118a engaging the open bottom of upper portion, bottom walls 118b engaging the open top of the lower portion, and a cylindrical waist 136 (in one embodiment) engaging walls 118a/118b. Walls 118a/118b may be flat, cone shaped or any appropriate shape (but are typically sloped). By providing a narrow portion, the vertical dimension (longitudinal) dimension of a given fluid displaced by the piston moving upward in the lower portion is magnified. That is to say, one milliliter of fluid displaced upward in the lower portion would become "taller" as it is constricted in a vertical dimension by movement of the fluid up through the constricted walls. Thus, a thin layer, such as a buffy coat layer BC, between a red blood cell RBC layer and plasma P, below and above buffy coat, respectively, may be exaggerated (see FIG. 4), when BC comes up into the narrowed portion and lies adjacent a side port 138. This allows easy withdrawal of any selected portion by positioning the layers post-centrifuge.

In one embodiment (see FIGS. 2 and 5) of Applicant's cup 112, the side port 138, which includes walls adapted to engage a concentrate collection syringe 150 for concentrate out (see FIG. 5), is adapted to be located near the bottom of waist 136, where it engages or lays adjacent the open apex of walls 118b. In this manner, for example, plasma, buffy coat or any other selected fluid may be drawn off through side port 138. For example, when a buffy coat layer reaches the lower edge of side port 138, it may gravity feed out or suction be fed out into a collection syringe 150.

Figure 2:
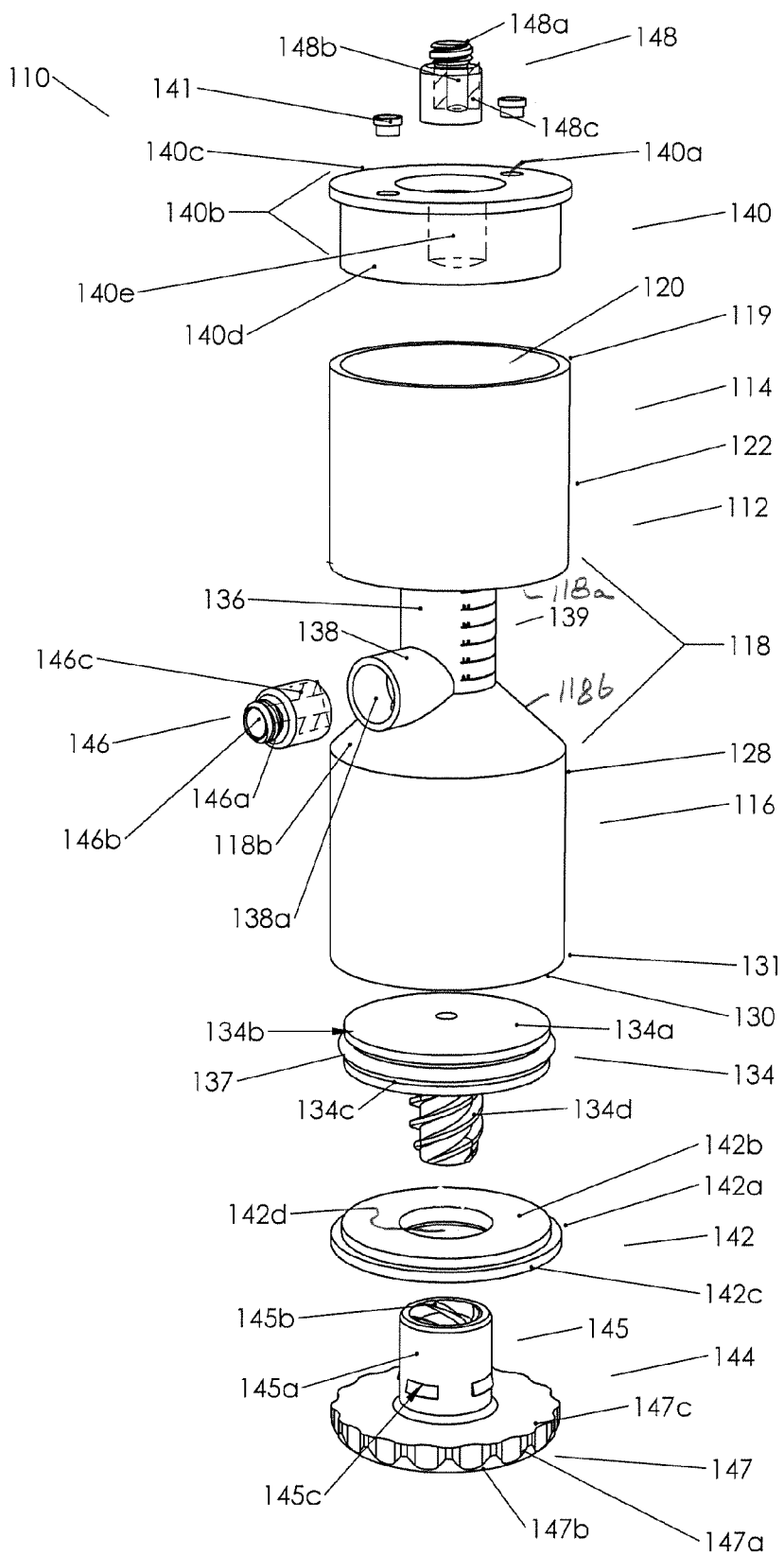
FIG. 2 is a perspective view of Applicant's fluids concentration cup assembly.
Figure 5:
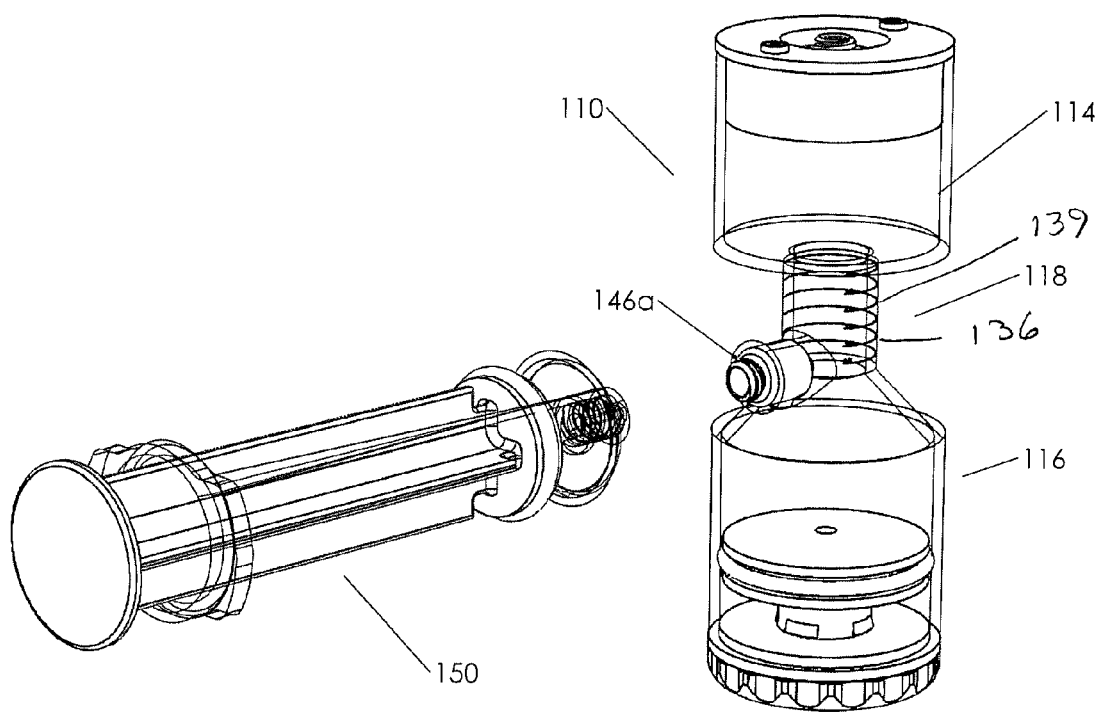
FIG. 5 illustrates a manner in which a syringe or other concentrated fluid collection device may engage the side port for selective removal of a fluid layer from a centrifuged aspirate.

As seen in FIGS. 2 and 5, scale lines or other indicia 139 are seen marked along the side of the outer walls of the container, including waist 136. They may be used to determine the volume of fluid and of the respective portions of separated concentrate. It will be seen that the gap between fluid markings will be spaced apart more where the volume is narrower or narrows, as the vertical axis if magnified of a fluid volume as it moves from the lower portion of the cone into the waist portion.

Figure 4:
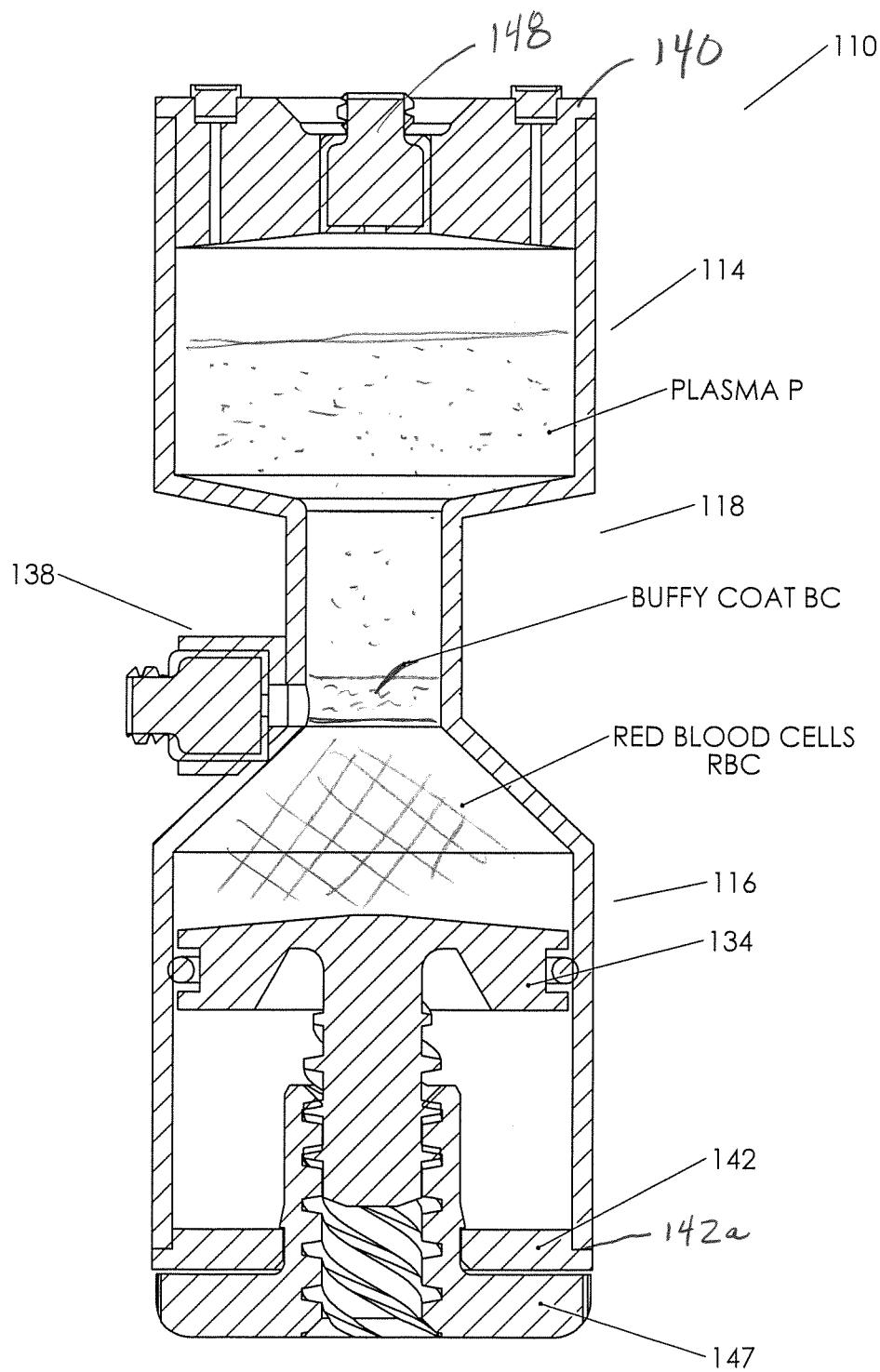
FIG. 4 is a sectional view of Applicant's fluid concentration cup assembly showing a selected intermediate layer, following centrifuging, for removal through a side port thereof.

In a preferred embodiment, the volume of the cup in the space between a bottom surface 140b of a lid 140 and an upper surface 134a of piston 134 when the piston is in the collapsed, lowered or Bottom Dead Center (BDC) position is about 80 ml. With this volume, sufficient aspirate (or other biological fluid to be centrifuged) may be received through the lid as set forth herein, for example, about 60 ml. Note that this may leave an air space of about 20 ml, in one embodiment, above the surface of the aspirate and of the concentrated fluids, so as to allow the piston to be driven upward so as to place the bottom of the buffy coat adjacent side port 138 as seen in FIG. 4. In a preferred embodiment, waist portion 136 has a volume of about 2-10 ml or about 4-8 ml, preferably 6 ml, and a diameter of about 0.778 inches.

In one method of use, pre-centrifuge, the piston is placed in a low position and an undifferentiated biological fluid is added through the lid by way of a syringe. The unit is then placed in a centrifuge cup and spun until the fluid separates and then it is removed. Upon removal, the piston is raised until a selected layer, such as a buffy coat layer, is adjacent the side port typically with the red blood cells below the side port. A collection syringe is attached to the Halkey and the buffy coat withdrawn. A typical 60 ml of aspirate (in one case) may yield about 2 ml or less of buffy coat. This buffy coat (or other selected fluid) will be placed in the narrow portion, typically the cylindrical waist, and withdrawal may commence, drawing the selected fluid out the side port.

Lid 140 is seen to have one or more vents 140a therethrough that may be sealed with vent caps 141. Vents will vent a pressure differential across the lid. Lid 140 is typically sealingly engaged, as by gluing or the like to open top 120. Rim 140b of lid 140 is seen to be notched so as to engage rim 119 of open top 120. Upper surface 140c of the lid may be flat and lower surface 140d may be slightly concave, as best seen in FIG. 3B. Having a concave lower surface 140d will mean that the entire assembly 110 may be inverted and a Halkey 148 with channel 148b therethrough may act as a drain to drain fluids from within the cup. Halkey 148 may have a threaded section 148a for engagement with a syringe 152 (see FIGS. 6A and 6B). Halkey 148 may also have a foam 148c, which may act as a fluid barrier under neutral pressures but, under increased pressures, as by that provided by a syringe 152 attached to threaded section 148a, will be responsive with fluid flow therethrough.

As seen in FIG. 2, side port 138 is seen to include walls defining a channel 138a. Channel 138a is open to the space within narrow portion 118 and is typically dimensioned to receive snugly and fluidly sealing a Halkey valve 146 (a fluid device interface) therein. Halkey 146 may include foam 146c, a threaded portion 146a for engagement with syringe 150 (see FIG. 5). A channel 146b in Halkey 146 is provided for withdrawal of fluids through side port 138. The side port is removably sealed, as by cap 143 (see FIG. 8A) threadably engaging threaded portion 146a. For example, cap 143 may be positioned snugly against the Halkey when assembly 110 is in a centrifuge. Similarly, a cap (not shown) may removably engage threaded portion 148a of Halkey 148. An alternate embodiment of side port 138 as seen in FIGS. 7-11 illustrate the use of a Halkey adapter 160 to engage Halkey 146 to channel 138a. Details of this embodiment are set forth below.

Figure 3:
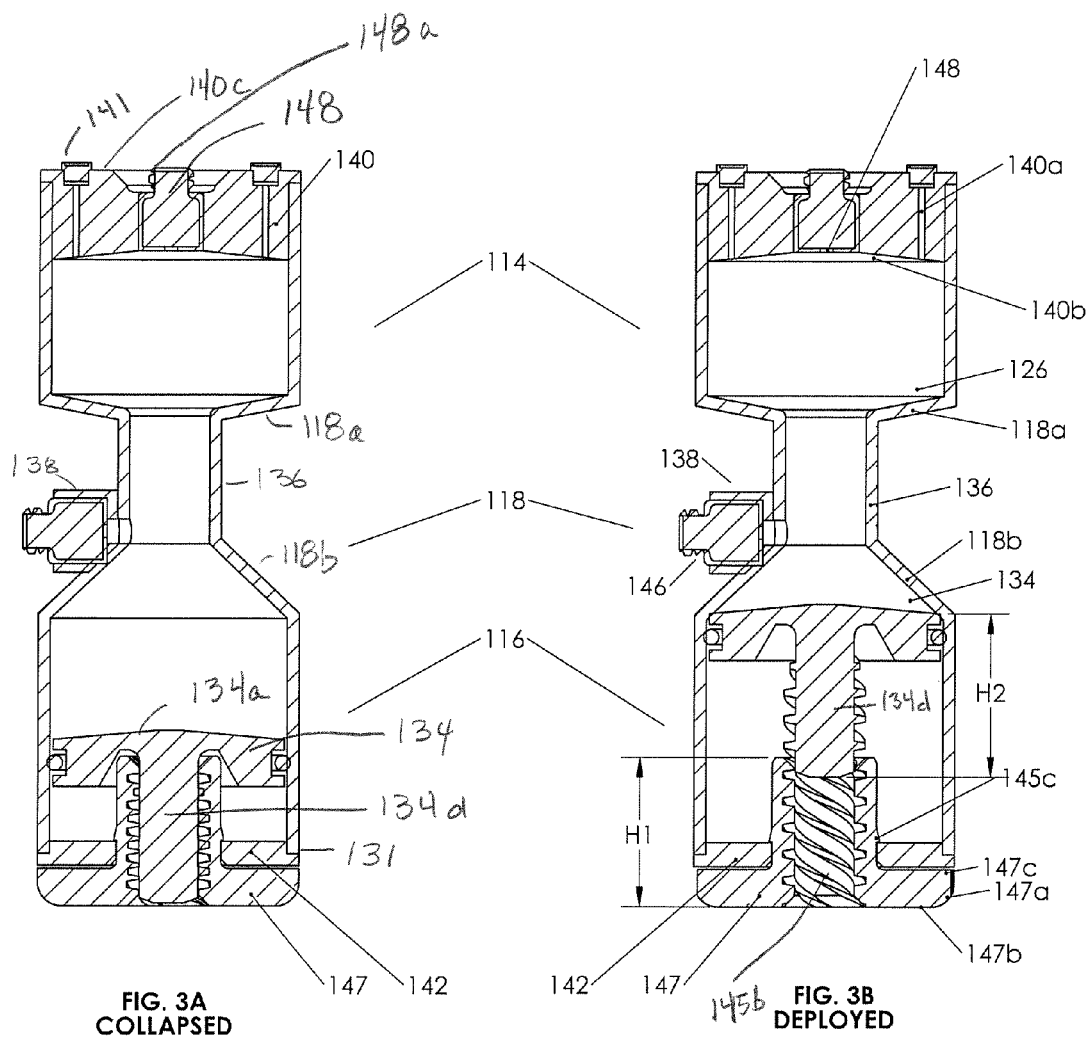
FIGS. 3A and 3B are sectional views of Applicant's fluids concentration cup assembly with the piston in a collapsed and deployed position, respectively.

Turning now to FIGS. 2-4, it is seen that a bottom plate 142 may be sealingly engaged to bottom rim 131 of open bottom 130 of lower portion 116. More specifically, it is seen that a notched rim 142a may fit snugly such that an upper surface 142b of the rim effectively seals the open bottom accepting a central opening 142d in the bottom plate 142. Central opening 142d extends between upper surface 142b and lower surface 142c. Central opening 142d is seen to engage a vertical neck 145 of a captured piston drive screw 144 which, along with drive piston 134, constitutes a drive assembly for driving the piston upward or downward in the lower portion 116 (see, for example, FIGS. 3A and 3B). That is to say, piston 134 may be driven between the collapsed (lower) and deployed (upper) positions (FIGS. 3A and 3B, respectively) by rotation of a base 147. Piston drive screw 144 is captured on bottom plate 142 as by the action of resilient wedges 145c (see FIG. 3B, for example). Wedges 145c ride on top surface 142b of the bottom plate 142 when the base 147 is rotated. Base 147 may have a notched rim 147a which dimension is typically not greater than the diameter of lower portion 116. Base 147 typically has a flat bottom surface 147b and a flat top surface 147c, and is integral with vertical neck 145. Neck 145 typically has an outer surface 145a and a threaded inner surface or threaded inner walls 145b.

Turning to piston 134, piston 134 is seen to have upper surface 134a, lower surface 134c, and a rim 134b. Rim 134b may include a cup shape portion for receipt of an elastomeric O-ring 137 (preferably two, see FIG. 7) thereon and piston 134 with O-ring thereon is dimensioned to be fluidly sealing and slidably received within the lower portion 116, such that the O-ring contacts the inner walls and slides up and down thereon between collapsed or lowered (FIG. 3A) and deployed or raised (FIG. 2B) positions. Upper surface 134a of piston 134 may be flat or domed (see FIG. 7), and lower surface 134c may be flat or recessed (see FIG. 8A) or suitably shaped. Threaded member 134d extends downward into engagement with threaded inner walls 145b of neck 145 of the piston drive screw 144.

Figures 6A, 6B:
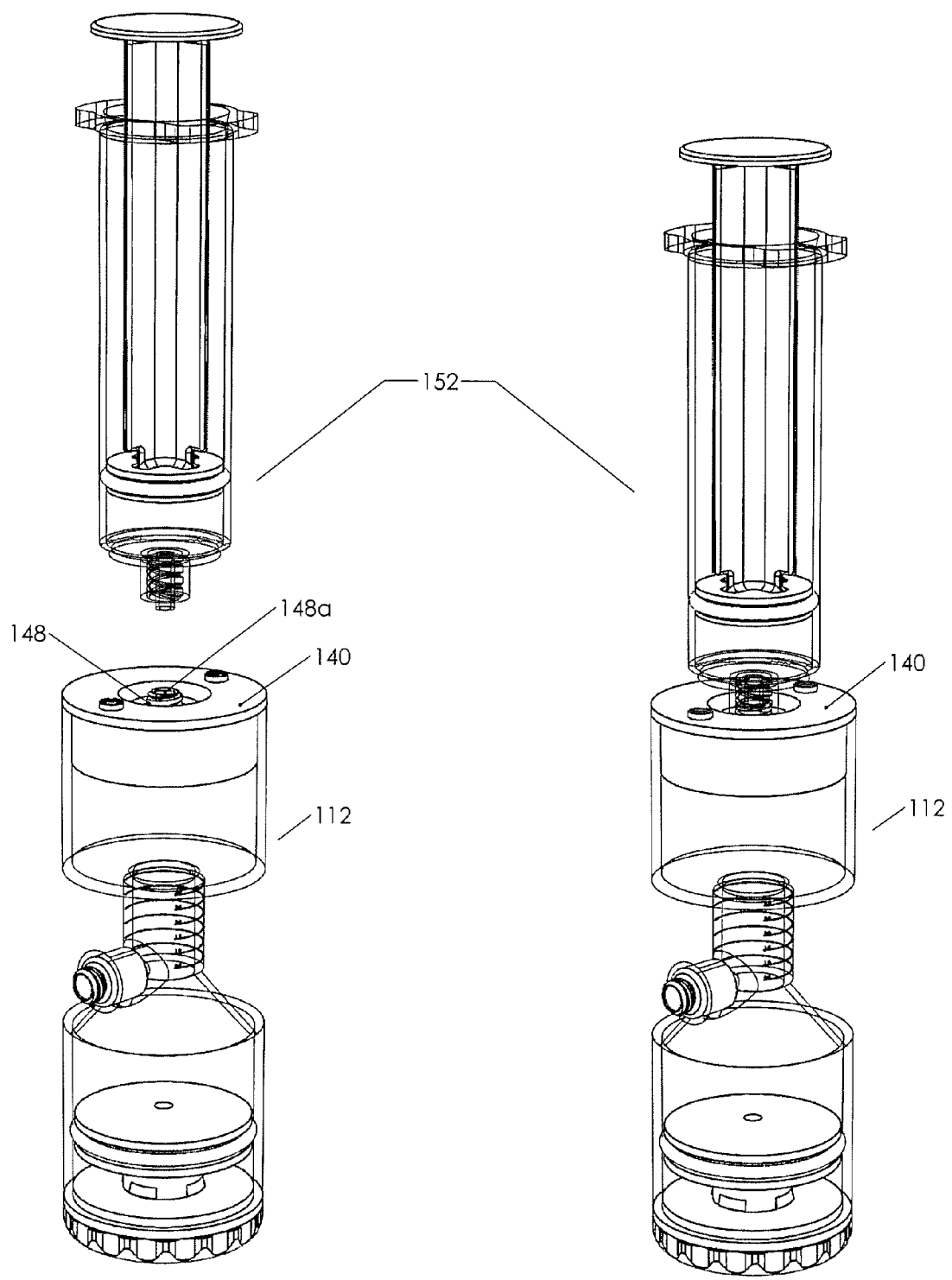
FIGS. 6A and 6B illustrate perspective views of Applicant's cup assembly showing the manner in which a syringe may transfer an aspirate to the cup assembly.

FIG. 4 illustrates the use of the fluids concentration cup assembly 110. Typically, the piston will be in the collapsed or lowered position when bone marrow aspirate or other fluid is received through the lid (see FIGS. 6A and 6B). After centrifuging, the piston may be deployed as seen in FIG. 4 to place, for example, the bottom surface of the buffy coat layer adjacent the side port 138. Withdrawal syringe 150 may be used to engage threaded portion 146a of Halkey 146 as seen in FIG. 5 to withdraw the buffy coat. FIGS. 6A and 6B illustrate the use of a second or aspirate carrying syringe 152 to transfer a bone marrow aspirate or other fluid, before centrifuging, into the cup 112 by engagement of syringe with Halkey 148 in lid 140.

Figure 7:
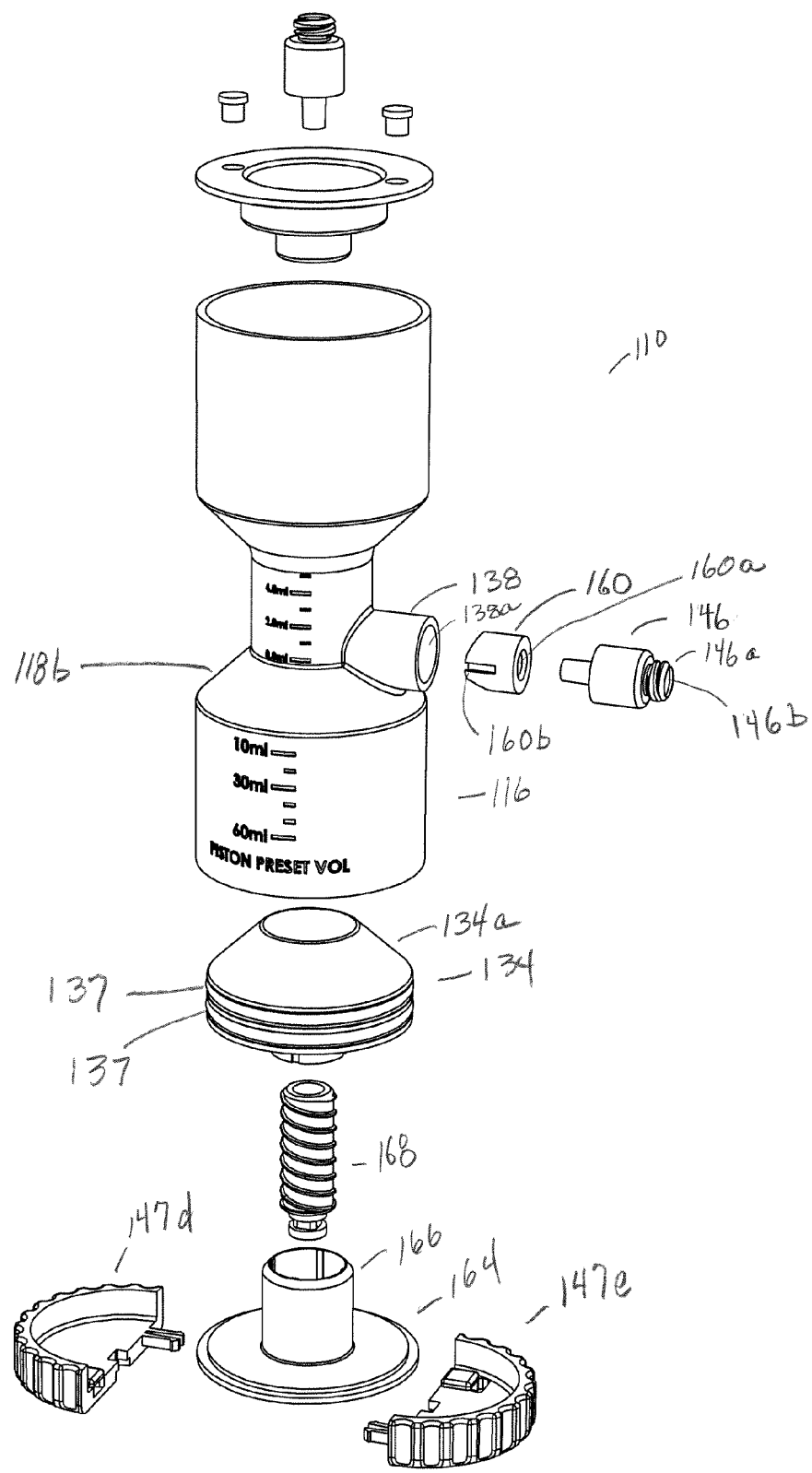
FIG. 7 illustrates an alternate preferred embodiment of Applicant's device in an exploded perspective view.
Figure 8A:
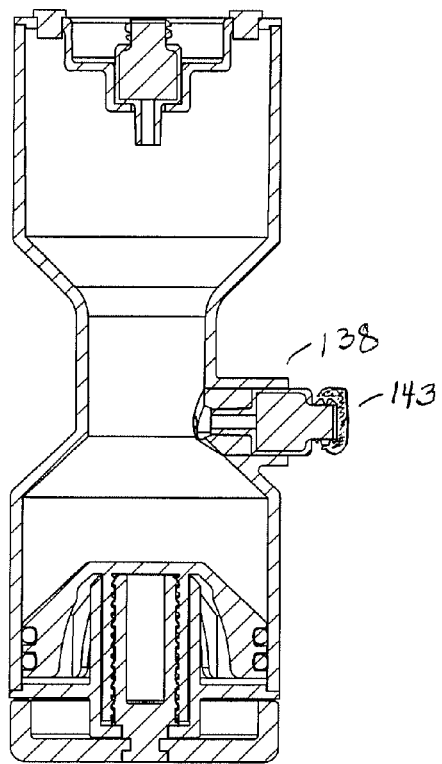
FIGS. 8A and 8B illustrate cross sectional elevational views of alternate preferred embodiments of Applicant's device with a piston in a collapsed or lowered position (FIG. 8A) and a raised or upper position (FIG. 8B).
Figure 8B:
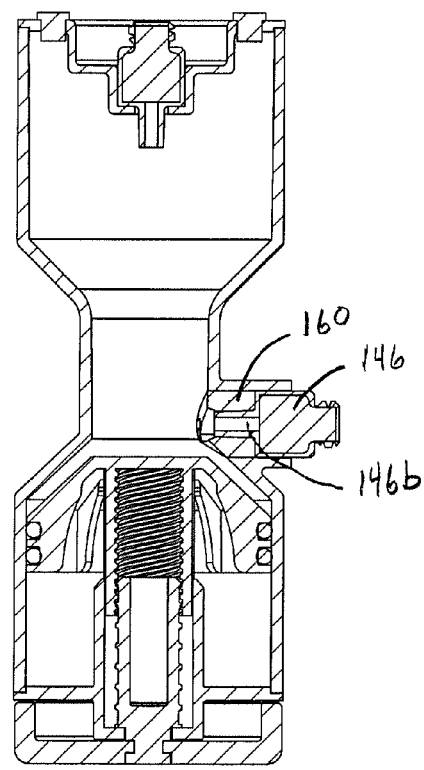
Figure 9A:
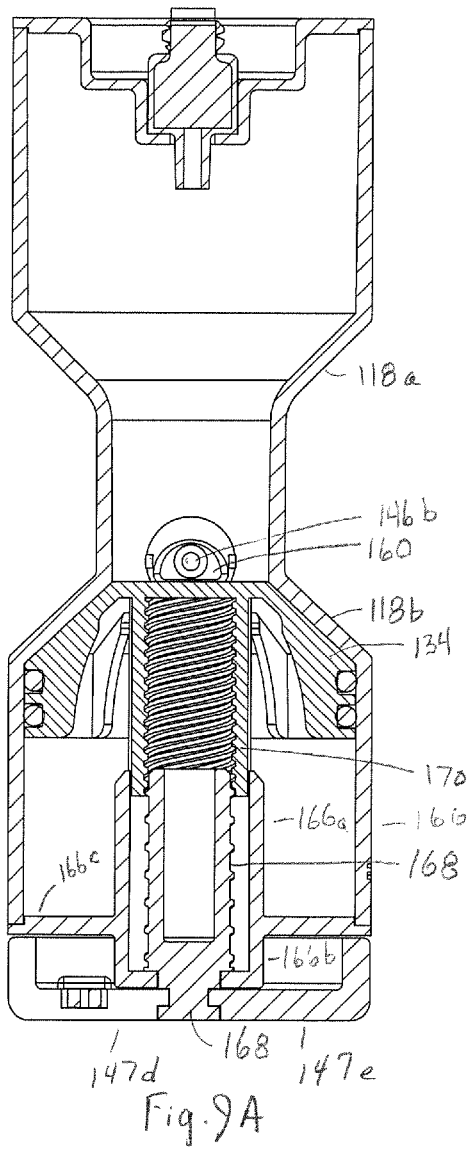
FIGS. 9A and 9B are cross sectional views illustrating an alternate preferred embodiment of Applicant's present invention showing the relationship of the piston to the walls of the container and the side port with the piston in the up position.
Figure 9B:
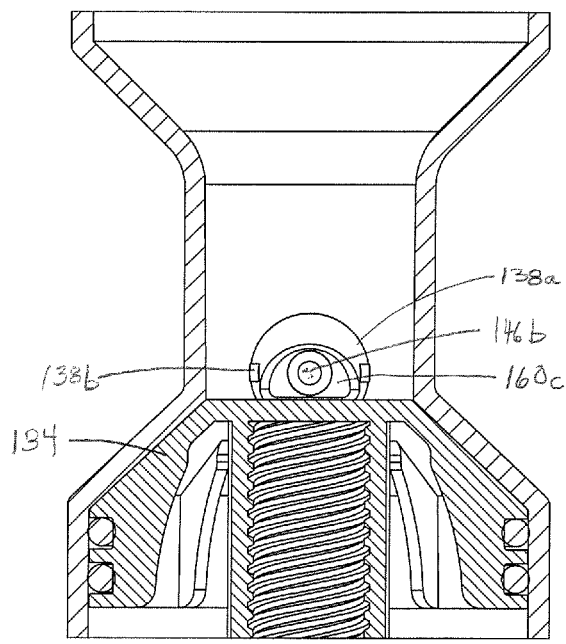

FIGS. 7, 8A, and 8B illustrate that the upper surface of 134a of piston 134 may be dome or conically shaped, such that it fits within conical or sloped walls 118b in a snug relationship when the piston is at top dead center (TDC) (see FIG. 9A). The dome shape of the piston is seen to be a truncated conical shape with a flat top surface that will lay above the lowest most portion of channel 38a/138a (see FIGS. 9A and 9B). The flat top portion of the piston is seen relationally to the bottom of the side port channel and, when the two are close, it allows for the efficient withdrawal of the buffy coat (or other liquid) as the buffy coat rests on top of the red blood cell and below the plasma, after whole blood has been centrifuged.

In a preferred embodiment, the narrow portion 18/118 includes sloped upper walls on 116 and sloped lower walls on 114, which meet at a cylindrical waist portion 136. The side port 138 has a channel 138a, which is typically cylindrical and whose lowermost portion is right at the top of where the cone portion adjacent open top 132. Walls 118a of narrow portion 118 may be angled downward from the horizontal in a range of 20-60°, most preferred 40-50°, and most preferred about 45° from the horizontal. The cup may be made of rigid polycarbonate, especially a clear hydrophobic polycarbonate and may have a height of about 4.875 inches or a preferred range of 3½ to 5¼ inches. The waist portion 136, in a preferred embodiment, is cylindrical and has a volume preferably between about 2 and about 10 milliliters, more preferred about 5 to about 7 milliliters, and most preferred about 6 milliliters.

When the piston is at top dead center and bottom dead center, the dimensions set forth in the table may be used, as measured from the upper surface of the piston to the bottom of the tip of the lid.

| CUP VOLUME mL (to lowest part of lid) | | |
| --- | --- | --- |
|  | Piston at TDC | Piston at BDC |
| Broadest Range (approx . . . ) | 5-25 mL | 10-80 mL |
| Next (approx . . . ) | 7-20 mL | 35-65 mL |
| Preferred (approx . . . ) | 10-15 mL | 45-60 mL |

In a method of use, a surgeon or other healthcare professional withdraws a bodily fluid, such as whole blood or bone marrow aspirate. The piston is set at BDC and the undifferentiated fluid is injected into the cup through the lid. The cap is centrifuged and then removed. At this point, the user will adjust the bottom of the piston, such that, after centrifugation, the bottom of the buffy coat layer will typically be near the preferred level for withdrawal.

FIGS. 7-11 show a Halkey adapter 160 with facing walls 160c with a mouse hole shape (see FIGS. 9A and 9B), such that fluid is funneled into channel 146b of Halkey 146. FIGS. 9A and 9B also show how channel 146b in the Halkey adapter 160 meets the piston top in flush relation when the piston is in the raised position. It is seen how fluid withdrawn through Halkey 146 (arrows in FIG. 11) is funneled to the channel by the sloped facing walls 160c.

FIGS. 7-11 illustrate an alternate embodiment adapted to help channel a selected fluid, post-centrifuge, into channel 146b of Halkey 146. While the term "channel" is used, a Halkey valve typically, does not have a visible channel under neutral pressure. Indeed, it appears to be filled with a foam-like substance. However, when a pressure differential of a set value is exceeded on the Halkey, such as by a syringe device in withdrawing the fluid from the cup, a channel is provided for a fluid to pass through. More information regarding the Halkey may be found at www.halkeyroberts.com. One Halkey that may be used, with this assembly, is Halkey Roberts Part No. e.245501024 (a bondable, one or two-way needleless valve). In any case, a nose of the Halkey will fit in channel 160a through Halkey adapter 160 to hold the Halkey in place and grooves 160b on either side of the side walls will engage ridges 138b on either side of channel 138a, so that Halkey 146 fits snugly to Halkey adapter 160 and the adapter is glued or otherwise affixed in the channel such that the facing walls 160c (see FIGS. 9A, 9B, and 11) place the lower edge of channel 160a adjacent (or just above) the upper flat top of piston 134 when piston 134 is at top dead center. Facing walls 160c are funnel-shaped (see FIG. 11), acting to funnel fluid going through Halkey 146 into channel 146b. This allows for a smooth, non-turbulent and complete flow of liquid above the piston top when it is at top dead center to flow through channel 146b into a collection device, such as a syringe 150, attached to threaded portion 146a (see FIG. 11).

Figure 10:
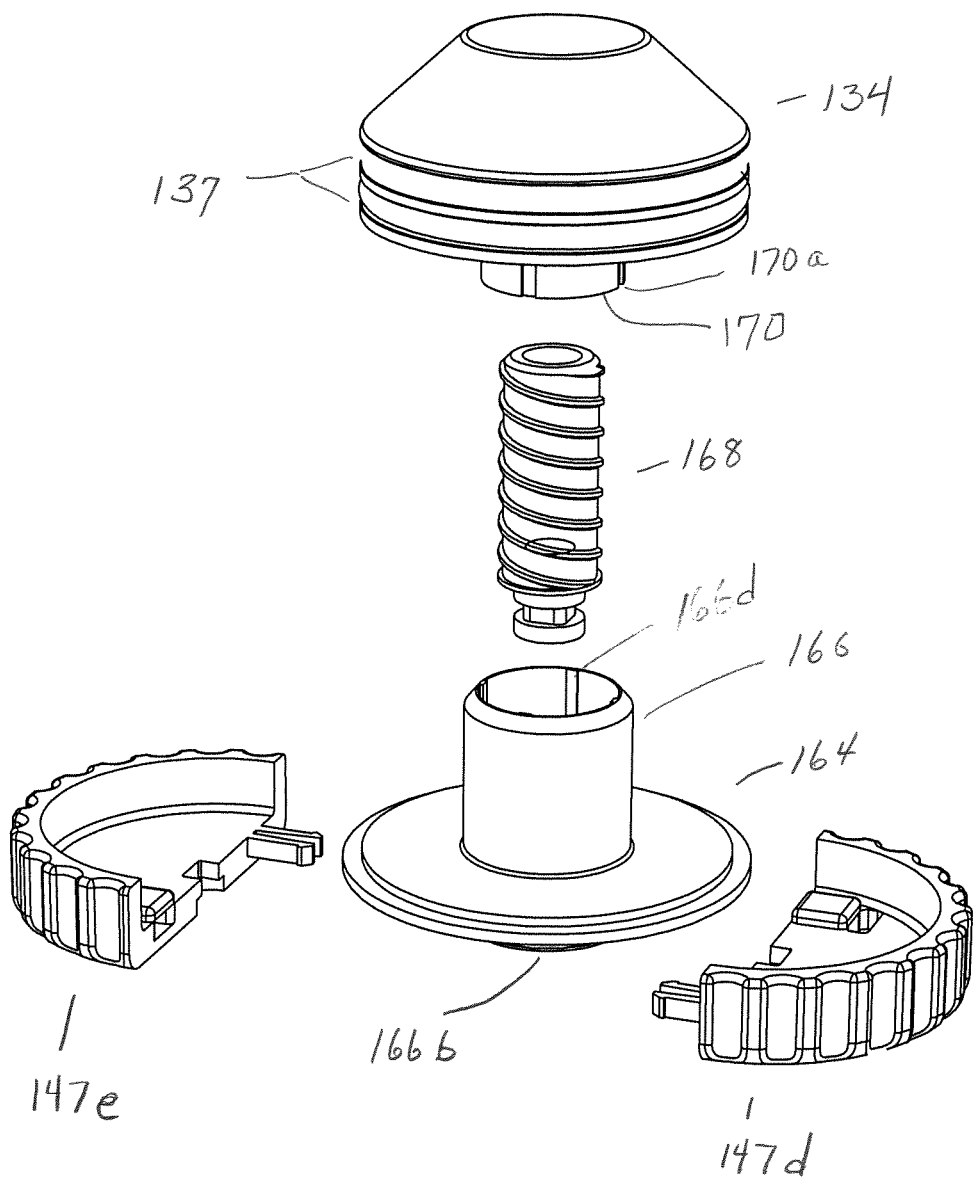
FIG. 10 is an exploded perspective view of an alternative preferred embodiment of a piston drive mechanism having an anti-rotation feature.
Figure 11:
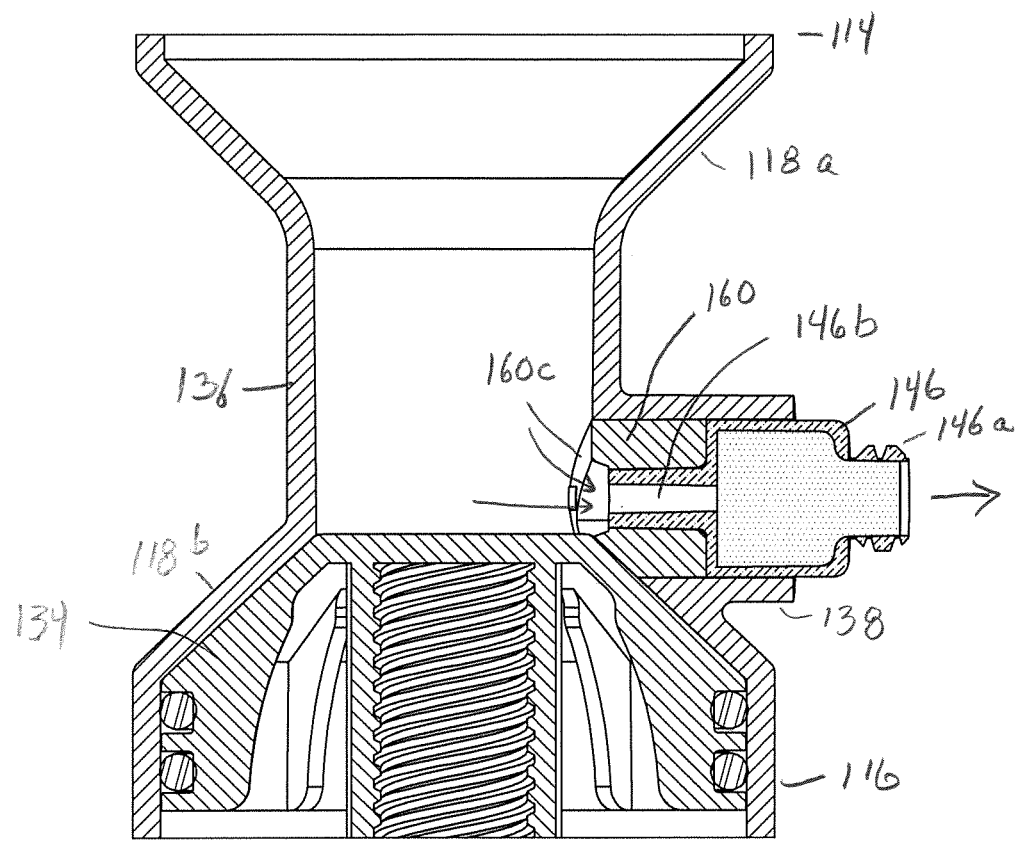
FIG. 11 is a cross sectional view showing the relationship of the Halkey, the Halkey adapter, the side port of the narrow portion and the piston top.

FIGS. 7-11 illustrate an alternate preferred embodiment of a drive piston assembly for moving the piston 134 longitudinally in the cup. Here, base 147 is seen to be split into two halves 147d/147e that are both manufactured in the same mold (so there is no left or right) and may clip together with resilient prongs and slots as seen in FIGS. 7 and 10. Lid 164 is seen to have a neck 166, the lid for sealing the bottom of the cup as by gluing, for example. Threaded section 168 is rigidly attached to base 147d/147e and is seen to engage an inner depending threaded leg 170 (see FIG. 9A) attached to the bottom of the piston. Threaded leg 170 has threads on inner walls thereof. Threaded section 168 is glued or otherwise affixed to base halves 147d/147e as in FIG. 9A, so that rotation of base 147d/147e causes threaded section 168 (which couples with the thread on threaded leg 170) to rotate, moving piston 134 up and down. Neck 166 of lid 164 is seen to have an upper portion 166a and a lower portion 166b that may be above and below a flat portion 166c. Flat portion 166c may have a notched perimeter as seen in FIG. 9A, the notched perimeter for engaging (fluid tight) the bottom rim of the cup. Outer walls of upper portion 166a snugly and telescopically engage the outer walls of threaded leg 170, which is seen to be partly recessed in recessed portion on the underside of piston 134. Multiple anti-rotation ridges 166d on the cylindrical inner surface of neck 166 project inward and longitudinally and engage multiple anti-rotation grooves 170a on the outer surface of threaded leg 170, such that rotation of the base and threaded section 168 will force the piston to go up and down and prevent it from rotating (a piston anti-rotation feature). The only structure that rotates in this embodiment is base 147 and threaded section 168 of the base. The structure that moves up and down is piston 134 and threaded leg 170. Thus, threaded members of the piston and rotatable base couple, as do anti-rotation members.

Although the invention has been described with reference to a specific embodiment, this description is not meant to be construed in a limiting sense. On the contrary, various modifications of the disclosed embodiments will become apparent to those skilled in the art upon reference to the description of the invention. It is therefore contemplated that the appended claims will cover such modifications, alternatives, and equivalents that fall within the true spirit and scope of the invention.

The invention claimed is:

1. A biological fluids concentration cup assembly comprising:
a rigid cup with an open top, an open bottom, and outer and inner walls;
a lid configured to engage the open top and to removably receive a device selected from the group consisting of a syringe and a fluid injection device;
wherein the cup has an upper portion, a lower portion, and a narrow portion between the upper and lower portion, and wherein the narrow portion includes a side draw port for fluid removal adapted to be engaged with a fluid receiving vessel for removal of a fluid from the narrow portion of the cup assembly, and
a drive piston assembly wherein the drive piston assembly includes a drive piston slideably engaging at least part of the lower portion of the cup.

2. The assembly of claim 1, further including a bottom plate for engaging the open bottom of the cup and wherein the drive piston assembly includes a piston screw drive assembly for moving the drive piston longitudinally at least in the lower portion between a raised position and a lowered position.

3. The assembly of claim 2, wherein the drive piston of the drive piston assembly includes a perimeter for fluid sealing against the inner walls up the cup, an upper and a lower surface, and wherein the piston screw drive assembly includes a threaded member extending down from the lower surface of the drive piston, and wherein the piston screw drive assembly also includes a piston drive screw extending through the bottom plate to engage the threaded member.

4. The assembly of claim 3, wherein the piston drive screw is coupled to the bottom plate with a neck extending through an aperture in the bottom plate and wherein the piston drive screw has a base with a rim, the base laying outside the bottom plate and adjacent thereto.

5. The assembly of claim 3, wherein the perimeter of the drive piston includes at least a pair of O-rings.

6. The assembly of claim 1, further including a bottom plate with an aperture and a rim, the rim for fluid sealing the bottom plate to the open bottom of the cup and wherein the drive piston assembly includes a pair of cooperating, coupling threaded members, one engaging the drive piston, the other engaging the aperture in the bottom plate and a base such that rotation of the base drives the drive piston up and down in the cup.

7. The assembly of claim 6, wherein the drive piston assembly and the bottom plate include anti-rotation members to ensure the drive piston does not rotate.

8. The assembly of claim 1, wherein narrow portion has a top wall angled between about 20 and about 60 degrees.

9. The assembly of claim 1, wherein the narrow portion includes a waist portion that has a volume of about 2 to 10 ml.

10. The assembly of claim 1, wherein the maximum volume of the cup measured between a top surface of the drive piston and the lid is between about 10 and 80 ml.

11. The assembly of claim 1, wherein the walls of the narrow portion include a scale on walls thereof.

12. The assembly of claim 1, wherein the side draw port includes a Halkey valve.

13. The assembly of claim 1, wherein the side draw port includes walls at an exterior end thereof for engaging a concentrated fluid collection device.

14. The assembly of claim 1, wherein the narrow portion includes a waist portion and wherein the side draw port of the cup is proximate a lower end of the waist portion.

15. The assembly of claim 1, wherein the walls of the narrow portion includes a scale on walls thereof wherein the side draw port includes a Halkey valve; wherein the side draw port further includes walls at an exterior end thereof for engaging a concentrated fluid collection device; and wherein the side draw port of the cup is proximate a lower end of the narrow portion.

16. The assembly of claim 1, wherein the lid includes a channel for introducing fluid to the cup.

17. The assembly of claim 1, wherein the cup is made of clear plastic and includes a scale on the walls thereof.

18. The assembly of claim 1, wherein the drive piston includes a body having walls shaped to conform to the shape of the lower portion of the cup and an upper surface having walls shaped to conform to walls of a part of the narrow portion.

19. The assembly of claim 18, wherein the walls of the upper surface of the drive piston lay adjacent the side draw port when the drive piston is in a raised position.

20. The assembly of claim 19, wherein the side draw port includes a valve having a channel therethrough, the channel opening into the narrow portion and wherein the port includes sloped walls adapted to funnel fluid from an interior of the cup into the channel.

21. A biological fluids concentration cup assembly comprising:
- a rigid cup with an open top, an open bottom, and outer and inner walls;
- a lid configured to engage the open top and to removably receive a device selected from the group consisting of a syringe and a fluid injection device;
    - wherein the cup has an upper portion, a lower portion, and a narrow portion between the upper and lower portion, and wherein the narrow portion includes a side draw port for fluid removal adapted to be engaged with a fluid receiving vessel for removal of a fluid from the narrow portion of the cup assembly, and
    - a drive piston assembly wherein the drive piston assembly includes a drive piston slideably engaging at least part of the lower portion of the cup;
- further including a bottom plate with an aperture and a rim, the rim for fluid sealing the bottom plate to the open bottom of the cup and wherein the drive piston assembly includes a pair of cooperating, coupling threaded members, one engaging the drive piston, the other engaging the aperture in the bottom plate and a base such that rotation of the base drives the drive piston up and down in the cup;
    - wherein the drive piston assembly and the bottom plate include anti-rotation members to ensure the drive piston does not rotate,
    - wherein the narrow portion has a top wall angled between about 20 and about 60 degrees;
    - wherein the walls of the narrow portion include a scale on walls thereof;
    - wherein the side draw port includes walls at an exterior end thereof for engaging a concentrated fluid collection device;
    - wherein the drive piston includes a body having walls shaped to conform to the shape of the lower portion of the cup and an upper surface having walls shaped to conform to walls of a part of the narrow portion; and
    - wherein the walls of the upper surface of the drive piston lay adjacent the side draw port when the drive piston is in a raised position.

* * * * *